US008574213B2

(12) United States Patent
Thilly et al.

(10) Patent No.: US 8,574,213 B2
(45) Date of Patent: Nov. 5, 2013

(54) PROCESS FOR PREPARING A LYOPHILIZED MATERIAL

(75) Inventors: Jacques Thilly, Rixensart (BE); Christian Vandecasserie, Rixensart (BE)

(73) Assignee: Aseptic Technologies S.A., Les Isnes (BE)

( * ) Notice: Subject to any disclaimer, the term of this patent is extended or adjusted under 35 U.S.C. 154(b) by 0 days.

(21) Appl. No.: 13/507,571

(22) Filed: Jul. 11, 2012

(65) Prior Publication Data

US 2012/0283689 A1 Nov. 8, 2012

Related U.S. Application Data

(62) Division of application No. 11/718,034, filed as application No. PCT/EP2005/011623 on Oct. 25, 2005, now abandoned.

(30) Foreign Application Priority Data

Oct. 27, 2004 (GB) .................................. 0423861.4
Jan. 26, 2005 (GB) .................................. 0501651.4

(51) Int. Cl.
*A61B 19/00* (2006.01)
*A61M 5/32* (2006.01)

(52) U.S. Cl.
USPC ........................................................ 604/411

(58) Field of Classification Search
USPC ................................................ 604/403–416
See application file for complete search history.

(56) References Cited

U.S. PATENT DOCUMENTS

| | | | |
|---|---|---|---|
| 1,769,941 | A | 7/1930 | Miller |
| 2,353,986 | A | 7/1944 | Barr |
| 2,380,339 | A | 7/1945 | Siedentopf |
| 2,783,908 | A | 3/1957 | Winfield |
| 3,286,366 | A | 11/1966 | Seligman |
| 3,474,543 | A | 10/1969 | Bender et al. |
| 3,810,469 | A | 5/1974 | Hurschman |
| 4,243,150 | A | 1/1981 | Gunne et al. |
| 4,275,511 | A | 6/1981 | Parkinson et al. |
| 4,564,054 | A | 1/1986 | Gustavsson |
| 5,219,083 | A | 6/1993 | Liebert et al. |
| 5,303,835 | A | 4/1994 | Haber et al. |
| 5,522,155 | A | 6/1996 | Jones |
| 5,740,654 | A | 4/1998 | Manni et al. |

(Continued)

FOREIGN PATENT DOCUMENTS

| | | |
|---|---|---|
| GB | 450 147 | 7/1936 |
| WO | WO 2004/085278 | 10/2004 |

OTHER PUBLICATIONS

Office action from the Patent Office of the Russian Federation in Application No. 2007115540/06(016882), which is a National Stage filing from PCT/EP2005/011623 by Thilly, 3 pp. (Jun. 11, 2009).

*Primary Examiner* — Philip R Wiest
(74) *Attorney, Agent, or Firm* — Klarquist Sparkman, LLP

(57) ABSTRACT

A process for preparing a lyophilized material, providing a container having a penetrable envelope and containing the material in a carrier liquid, whereby the penetrable region is penetrated with a penetrator which provides a conduit through the envelope, and the carrier liquid is evaporated out of the container via the conduit, after which the penetrator is withdrawn.

3 Claims, 8 Drawing Sheets

(56) References Cited

U.S. PATENT DOCUMENTS

Figure 1:
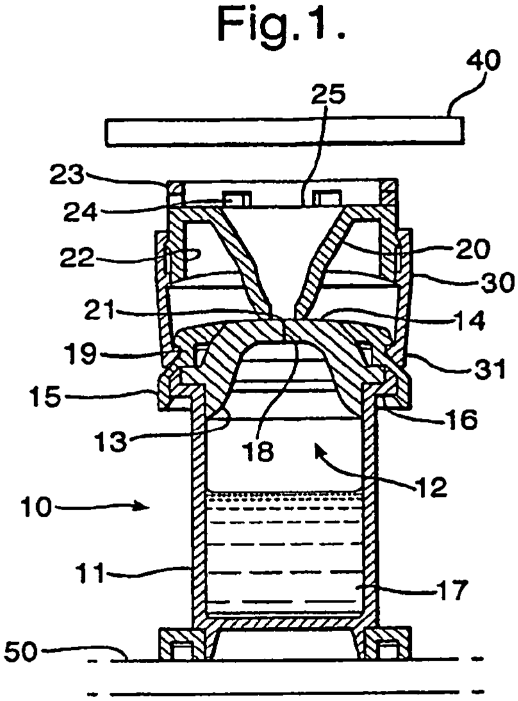

| | | | | |
|---|---|---|---|---|
| 6,090,093 | A | 7/2000 | Thibault et al. | |
| 6,237,649 | B1 | 5/2001 | Moisio et al. | |
| 6,604,561 | B2 | 8/2003 | Py | |
| 6,695,829 | B2 * | 2/2004 | Hellstrom et al. | 604/415 |
| 2005/0224137 | A1 | 10/2005 | Tribble et al. | |
| 2006/0266431 | A1 | 11/2006 | Thilly et al. | |

* cited by examiner 43
44
45A
45B
45C
45D
45E
46
47
48
49
410
10
40
41
42

100
101
102
103
104
105
106
107
108
10
13
15

PROCESS FOR PREPARING A LYOPHILIZED MATERIAL

CROSS REFERENCE TO RELATED APPLICATION

This application is a divisional of U.S. patent application Ser. No. 11/718,034, filed Apr. 26, 2007 now abandoned, which is the U.S. National Stage of International Application No. PCT/EP2005/011623, filed Oct. 25, 2005, which claims the benefit of Great Britain Patent Application No. 0423861.4, filed Oct. 27, 2004 and Great Britain Patent Application No. 0501651.4, filed Jan. 26, 2005. The foregoing applications are all incorporated herein by reference.

This invention relates to a process for providing lyophilized materials and to apparatus for use in such a process.

Lyophilization is a well-known process in the pharmaceutical and vaccines industries in which a dispersion, e.g., a solution or suspension, of a material in a carrier liquid, normally aqueous, is frozen then exposed to reduced pressure to cause the liquid to evaporate, e.g., to perform a sublimation transition from the frozen to the vapor state. This process makes it possible to withdraw water contained in a material to make the material more stable at ambient temperature and thus to facilitate its conservation. A typical lyophilization process is disclosed in EP-A-0 048 194.

Normally the dispersion is contained in a container typically a vial, which is exposed to the reduced pressure so that the liquid can evaporate out through an opening of the container, e.g., the open mouth of a vial. Vial closures are known which can be mated with a vial mouth in a first, upper, position leaving a vent for the escape of evaporating liquid, and which can be moved downward into a second position when the lyophilization process is complete to seal the vial. Typically vials with such closures in their upper, vented, position are arranged in a two dimensional array on a shelf for freezing and then exposure to a reduced pressure. Plural shelves are stacked vertically above each other with the underside of an upper shelf above the closures of vials on the shelf below, and when the lyophilization process is complete upper shelves are lowered onto the closures of vials on the shelf immediately below to push the closures into the lower closed position.

Numerous types of apparatus are known for performing the lyophilization process on such containers, generally comprising a chamber which can be hermetically closed with the containers inside and inside which suitable conditions of temperature and reduced pressure can be maintained.

A specific type of vial with a closure is disclosed in WO-A-04/018317 but is not disclosed therein for use in a lyophilization process.

Some problems of known lyophilization processes using the above described vials are that the mouth openings and vents of these known vials allow opportunity for ingress of contamination after a dispersion of the material has been introduced into the vial, e.g., during the subsequent stages of loading the vial containing the dispersion onto shelves suitable for the lyophilization apparatus and of transporting such vials to the lyophilization apparatus.

It is an object of the present invention to address these problems, and to offer further advantages, as will be disclosed below.

In a first aspect this invention provides a process for preparing a lyophilized material comprising:

providing a container bounded by an envelope having a penetrable region and containing a dispersion of the material in a carrier liquid, with the penetrable region penetrated with a penetrator such that the penetrator provides a conduit through the envelope to provide communication between the inside and outside of the container when the penetrator has penetrated the penetrable region, evaporating the carrier liquid out of the container via the conduit, withdrawing the penetrator from the penetrable region.

Such a process may be performed by providing a container bounded by an envelope having a penetrable region and containing a dispersion of the material in a carrier liquid, penetrating the penetrable region with the penetrator such that the penetrator provides a conduit through the envelope to provide communication between the inside and outside of the container when the penetrator has penetrated the penetrable region, evaporating the carrier liquid out of the container via the conduit, then withdrawing the penetrator from the penetrable region.

The container may be a vial, e.g., a typical pharmaceutical vial, made of glass or plastics material, having a mouth opening closed by an elastomeric closure, e.g., which plugs into the mouth opening, and the penetrable region may comprise a region of this elastomeric closure. In such a construction the combination of vial and closure comprise the said envelope.

Evaporation of the carrier liquid out of the container via the conduit may be by generally conventional lyophilization conditions, e.g., maintaining the dispersion at a temperature such that the carrier liquid is frozen, and application of reduced pressure so that the frozen liquid sublimates directly from the solid to the vapor state. Suitable conditions of temperature and reduced pressure are for example disclosed in the Example of EP-A-0 048 194.

By "penetrates" and derived terms as used herein is included at least partially penetrates, and the term includes opening a communication passage through the penetrable region, for example actual passage of the penetrator from one surface of the envelope to another, e.g., puncturing and physically disrupting of the envelope, expansion of an already existing hole by means of the penetrator, disruption of a weakened area of the envelope by the penetrator to create an opening through the envelope.

The penetrable region may comprise a previously-formed puncture hole. For example such a previously-formed formed puncture hole may have been formed by driving a puncturing means such as a needle through the penetrable region. Such a needle may be a hollow filling needle which has been passed through the envelope and via which the dispersion has been introduced into the vial, the needle then subsequently withdrawn, and the liquid so introduced may subsequently be cooled and frozen for lyophilization. For example such a needle may be passed through the elastomer closure of a vial. Typically with a suitable thickness of the elastomer material of the closure the elastic nature of the closure causes the elastomer material to close when the needle has been withdrawn, to thereby close the residual needle hole sufficiently to reduce the possibility of contaminants entering the vial via the puncture hole before the hole can be sealed. This offers the advantage that after introducing the liquid into a vial using a filling needle there is much less opportunity for contamination to enter the vial than would be the case with the above-mentioned known vial in which, after a liquid has been introduced into the vial, the closure is inserted into the vial mouth but in a partly open vented state. Also, advantageously after filling using such a filling needle and leaving a closed puncture hole the vial may be inspected through its transparent wall for particles, with less threat of contamination than would be with the known vials.

The process of the invention may therefore include the preceding step of providing the container bounded by an envelope having a penetrable region therein by passing a hollow filling needle through the envelope, introducing the dispersion into the container via this needle, then subsequently withdrawing the needle to leave a residual puncture hole in the closure. Preferably such a filling needle has a pyramidal point, as it is found that such a needle cuts a hole in controlled directions. Preferably such a pyramidal point has three faces to cut the hole in three controlled directions. A preferred construction of such a filling needle is for example disclosed in W02004/096114.

Figure 6:
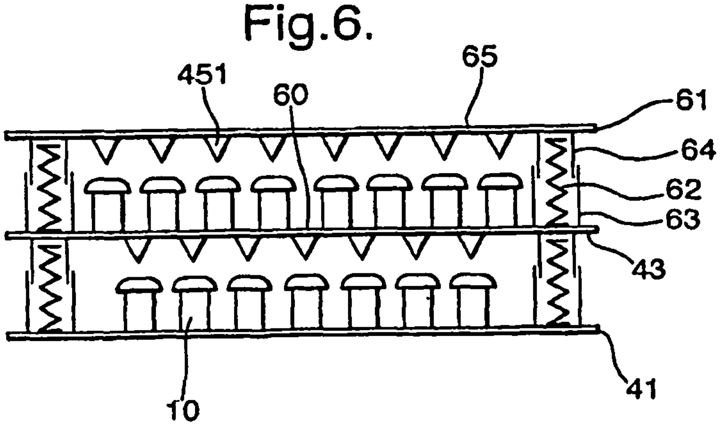

A suitable construction of such a vial arid closure is that disclosed in WO-A-04/018317, specifically as disclosed in and with reference to FIG. 6 thereof. Such a vial has an upwardly-facing mouth opening bounded by a rim, and a closure system comprising an elastomer closure part shaped to sealingly engage with the mouth opening, having a lower surface facing the interior of the vial and an opposite upper surface facing away from the vial, and capable of being punctured by a needle, and a clamp part able to engage with the vial, particularly with the rim of the mouth opening, and able to bear upon the upper surface of the closure part to hold the closure part in a closing relationship with the mouth opening, the clamp part having an aperture therein through which a region of the upper surface of the closure part is exposed when the clamp part is engaged with the vial.

In this embodiment the said exposed region of such an elastomeric closure, suitably when previously punctured by a needle as described above, may comprise the penetrable region. An advantage of such a vial is that it may be provided sealed by the closure and with a sterile interior, e.g., sterilized by radiation, or for example when made in a sterile state by the manufacturing process disclosed in W02005/005128.

The process preferably comprises the further step of sealing or otherwise covering the penetrable region after the penetrator has been withdrawn from the penetrable region.

In another aspect the invention provides apparatus suitable for use in the process described herein comprising:

a penetrator capable of penetrating a penetrable region of a container bounded by an envelope having a penetrable region therein and containing a dispersion of the material in a carrier liquid such that the penetrator when penetrating the penetrable region provides a conduit through the envelope to provide communication between the inside and outside of the container when the penetrator has penetrated the penetrable region, means to cause the penetrator to penetrate the penetrable region, means to evaporate the carrier liquid out of the container via the conduit, means to withdraw the penetrator from the penetrable region.

Suitable embodiments of the process, containers suitable for use with the process, and the apparatus, and working relationships between them will now be described.

The penetrator may be suitable to form a hole or enlarge a pre-existing hole through the penetrable region of the envelope, e.g., through the elastomer closure of a vial. The penetrator may be shaped, e.g., in cross section, to provide a conduit through the envelope when the penetrator has penetrated the envelope. In an embodiment the penetrator may comprise a generally tubular member having an end adapted to penetrate the penetrable region, e.g., a pointed end. Alternatively the penetrator may have one or more concavity in its outer surface to provide such a conduit between the penetrator and the adjacent surface of the penetrable region. Typically such an end may be generally pointed. For example the penetrator may comprise a generally conical member, e.g., a hollow cone with an open base or an opening adjacent its base, and an opening adjacent its apex, with a conduit passing through the penetrator, e.g., linking the opening at the apex and the open base, such that its apex may penetrate the penetrable region and vapor of the carrier liquid may enter the apex, pass through the hollow interior of the cone and exit via the conduit. Such a conduit should be of suitable dimensions to allow flow of the vapor of the evaporating liquid at a sufficient rate that lyophilization can be achieved in an acceptable time, i.e., similar to known lyophilization processes, which will be known to those in the art. To achieve this, typically at its narrowest the conduit should have a cross section of at least 1 mm, preferably 2 mm or more.

The conduit may incorporate a barrier which is permeable to gases but obstructs the passage of particles and in particular of microorganisms to thereby reduce the likelihood of contamination entering the container. Such a barrier may comprise a thin permeable membrane, for example made of a sterile filtration media.

In a first embodiment of the process and apparatus of the invention, the penetrator may be mountable on the container, e.g., on a vial, so that the penetrator can be moved, suitably reciprocally, from a first position in which the penetrator is outside the container and does not penetrate the penetrable region, to a second position in which the penetrator penetrates the penetrable region, and preferably then back towards a first position in which the penetrator is outside the container and does not penetrate the penetrable region.

In one form of this first embodiment, the penetrator may be provided in combination with a guide whereby the penetrator may be mounted on the container.

Such a combination comprises a further aspect of this invention, comprising:

a penetrator adapted to penetrate a penetrable region of the envelope of a container to thereby provide a conduit through the envelope to provide communication between the inside and outside of the container when the penetrator has penetrated the penetrable region, and a guide which is mountable on the container to thereby support the penetrator so that the penetrator can be moved from a first position in which the penetrator does not penetrate the penetrable region to a second position in which the penetrator penetrates the penetrable region, and optionally back toward a first position in which the penetrator does not penetrate the penetrable region.

For example a guide may be removably mounted on the container, capable of supporting and guiding the penetrator for such movement. In an embodiment, particularly suitable for the above-mentioned generally conical penetrator, and particularly when the container is a vial with an elastomeric closure, the guide may comprise a generally cylindrical sleeve or part sleeve within which the penetrator is movable, suitably reciprocally.

In a preferred construction of this last-mentioned apparatus, the penetrator and the guide maybe made integrally, e.g., of plastics material by means of injection molding. In this construction the penetrator and guide may be so made initially linked by one or more thin frangible integral link and with the penetrator in the first position, so that as the penetrator is moved from the first position toward the second position severance of the link(s) occurs.

When the vial is of the above-mentioned type disclosed in WO-A-04/018317 such a guide may be mountable upon the vial by removable engagement with the clamp part. In a preferred type of vial disclosed in WO-A-04/018317 the clamp part is itself provided with means for engagement of a cover part, being the groove 37 disclosed in FIG. 1 of WO-A-04/018317, and the guide may engage in a snap-fit with such a groove. It may be preferable to engage such a removable guide with the container such as a vial before any liquid content in the vial is frozen, as engagement features such as a snap-fit engagement may become brittle and lose their resilience at the low temperatures normally used for freezing liquids in lyophilization processes.

The penetrator may be caused to penetrate the penetrable region by relative movement of the penetrator and the container such that the end adapted to penetrate the penetrable region contacts the penetrable region and penetrates it. For example if the penetrator comprises a tubular member with a pointed end or apex of a cone this may be a movement parallel to the longitudinal axis of the tubular member or base-apex axis of the cone.

This movement may be caused by application of a force to the penetrator to urge the penetrator in this direction. As mentioned above it is common practice in the art of lyophilization to arrange vials for exposure to a reduced pressure in a two dimensional array on a shelf, and to stack plural shelves vertically above each other for exposure. Therefore in the process the application of force to the penetrator to urge the penetrator in the first position toward the second position direction may be achieved by arranging containers, e.g., vials, in a two dimensional array on a shelf, then causing a member to bear upon the penetrator to urge the penetrator in this direction. Such a member may comprise part of a vertically upper adjacent shelf caused to bear upon the penetrator to urge the penetrator in this direction. During the process of evaporation of the liquid this member, e.g., upper shelf may bear upon the penetrator to maintain the penetrator in position.

The penetrator, and/or guide may incorporate suitable vent means, e.g., apertures so that contact of such a shelf with the penetrator does not impede outflow of vapor of the carrier liquid through the conduit.

In another form of this first embodiment a penetrator is provided which is itself mountable on the container, such as a vial, in a position in which the penetrator is penetrating the penetrable region, e.g., the elastomeric closure of a vial.

Such a penetrator may as above comprise a generally conical member, and may be made of plastics material by means of injection molding. Such a penetrator may be mountable on the container such as a vial by means of a snap fit engagement. When the vial is of the above-mentioned type disclosed in WO-A-04/018317 such a penetrator may be mountable upon the vial by removable engagement with the clamp part thereof, which as mentioned above is itself provided with means for engagement of a cover part, being the groove 37 disclosed in FIG. 1 of WO-A-04/018317, and the penetrator may engage in a snap-fit with such a groove. For example such a penetrator may comprise the conical member at least partly surrounded by a skirt extending in the cone base-apex direction, the skirt having snap-fit engagement means adjacent the rim furthest from the cone base. The conduit through the penetrator may be closed by a barrier membrane which allows gases to pass through but not particulate contaminants.

It may be preferable to engage such a penetrator with the container such as a vial before any liquid content in the vial is frozen, as engagement features such as a snap-fit engagement may become brittle and lose their resilience at the low temperatures normally used for freezing liquids in lyophilization processes.

In use this form of penetrator may be mounted, e.g., by the snap fitting onto a vial, penetrating the elastomeric closure so that the liquid may be evaporated from the vial, typically after being frozen solid. Thereafter the penetrator may be removed from its mounting on the vial. To facilitate the mounting of the penetrator on the container a mounting tool may be provided to bear upon the penetrator so that for example a snap-fit engagement engages. To facilitate the removal of the penetrator from the container a removal tool may be provided. In one construction snap fit means on the penetrator may be provided with a disengagement means, for example a pivot lever upon which the removal tool may bear to disengage the snap-fit engagement.

In a second embodiment of the process and apparatus of the invention, plural containers, e.g., vials, may be situated on an upward facing surface of a lower shelf, and a vertically adjacent upper shelf may comprise plural penetrators, and the upper and lower shelves may be moved relatively toward each other, so that the penetrators thereof are thereby moved reciprocally from a first position in which the penetrator does not penetrate the penetrable region, to a second position in which the penetrator penetrates the penetrable region, and back into a first position in which the penetrator does not at least partly penetrate the penetrable region.

An apparatus is therefore provided particularly suitable for this second embodiment of the process, comprising a lower shelf having an upwardly facing surface suitable for locating plural containers, e.g., vials, thereon, and a vertically adjacent upper shelf having a downward facing surface which comprises plural penetrators, the upper and lower shelves being movable relatively toward each other, so that the penetrators thereof are thereby moved from a first position in which the penetrator does not penetrate the penetrable region, to a second position in which the penetrator penetrates the penetrable region, and reciprocally back towards a first position in which the penetrator does not penetrate the penetrable region.

Such upper and lower shelves and the penetrators of this apparatus of the second embodiment may be made of metals suitable for lyophilization processes, e.g., stainless steel.

In this second embodiment the upper shelf may be moveable downwardly toward the lower shelf, or the lower shelf may be moveable upwardly toward the lower shelf, or the upper shelf may be moveable downwardly and the lower shelf may be moveable upwardly.

In this second embodiment each penetrator may comprise a generally conical member with its apex pointing downwardly from a lower surface of the upper shelf toward the lower shelf, e.g., a hollow cone with an opening adjacent its apex, and an open base, such that its apex may penetrate the penetrable region and vapor of the carrier liquid may enter the apex, pass through the hollow interior of the cone and exit via the open base, e.g., as described above. Such a penetrator may be made integrally with the upper shelf, or may be attached to the upper shelf.

This second embodiment of the apparatus may comprise an upper shelf having an upward facing surface on which are situated plural containers such as vials, and vertically adjacent to this first upper shelf there may be a further upper shelf which comprises plural penetrators above this upward facing surface, and this further upper shelf may be moved analogously to the upper shelf described above. The further upper shelf may itself have an upward facing surface on which are situated plural vials, so that plural such shelves may be stacked vertically relative to each other.

The weight of an upper shelf may be sufficient to maintain the penetrator, in both embodiments of the apparatus, in the second position penetrating the penetrable region, e.g., of an elastic closure against the elasticity of the closure, and/or upper and lower shelves may be held together during the evaporation procedure. Thereafter the upper and lower shelves may be moved relatively vertically apart so that the penetrator is moved toward the first position. The elasticity of an elastomeric closure can tend to urge the penetrator out of the second position.

When the weight of an upper shelf is used to hold the penetrator in the second position, penetrating the penetrable region, the elasticity of, e.g., an elastomeric closure may be insufficient to subsequently urge the penetrator from the closure back towards the first position. In such a situation means may be provided to move the upper and lower shelves relatively closer together and relatively further apart, and such means may be conventional means known for raising and/or lowering shelves. For example the vertically adjacent shelves may be resiliently biased toward the first position, for example by a spring means between them.

Force applied to the penetrator and/or restraint of movement of the penetrator, e.g., the weight of an upper shelf bearing downwards upon the penetrator, may be necessary to maintain the penetrator in the second position penetrating an elastic closure against the elasticity of the closure. When such force or restraint is released, e.g., by increasing the vertical separation between the lower and upper shelves until the upper shelf no longer bears on the penetrator, the elastic will tend to spring back to eject the penetrator from the closure. Increasing the vertical separation may be done whilst the elastomer closure is at the reduced temperature and then allowing the closure to warm toward ambient temperature, or alternatively the closure may be allowed to warm to ambient temperature before increasing the vertical separation.

The penetrator may be withdrawn from the penetrable region toward the first position by a movement of the penetrator relative to the container such that the end adapted to penetrate the penetrable region is withdrawn from the penetrable region. Suitable means to withdraw the penetrator from the penetrable region may use the elasticity of the elastomer material of a vial closure.

For example in processes and apparatus comprising a lower shelf upon which plural vials may be arranged in a two dimensional array, and a second shelf vertically above the first shelf and able to be moved downwardly, suitable means may comprise a means to move the upper and lower shelves apart. Such means may be generally conventional as used in lyophilization processes.

Alternatively the upper and lower shelves may be biased toward the above-mentioned first position.

When the process of the invention is a lyophilization process in which the dispersion is maintained at a temperature such that the carrier liquid is frozen, and sublimating the liquid directly from the solid to the vapor state under reduced pressure, at such reduced temperatures an elastomer as used for a vial closure is likely to become less elastic, hindering the ability of a penetrator to penetrate an elastomer closure. Therefore it is preferred that the penetrator penetrates such a closure before the liquid has been frozen by the reduced temperature. The elasticity of the elastomer material of a vial closure may be employed to move the penetrator back toward a first position in which the penetrator is outside the container and does not extend through the penetrable region. The elastic nature of such a closure will tend to close the penetration hole resulting from the penetration by the penetrator, and will tend to spring back to eject the penetrator from the closure. The elastomer material of a vial closure can become less elastic at lower temperatures. Therefore when the process of the invention is the above-mentioned lyophilization process it is preferred to allow the temperature of the closure to rise toward, preferably to, ambient temperature before withdrawing the penetrator, so that the elasticity of the closure is more effective.

When the evaporation operation is completed the pressure within the container may be returned to atmospheric by the ingress of a sterilized atmosphere, e.g., air or an inert gas (herein the term "sterile" and derived terms means any reduction of the level of undesirable matter such as micro-organisms etc. to a level which is acceptable in the field of lyophilized materials such as drugs or vaccines). This is preferably done before the penetrator is withdrawn so that such an atmosphere may enter the container via the conduit, and before the elastic closure of a vial has sprung back to close the puncture hole.

Suitably the apparatus also comprises means to reduce the temperature of the carrier liquid to a temperature at which it is frozen solid. Such means may comprise a hermetically sealable refrigerated enclosure in which the container and penetrator, and suitably the means to cause the penetrator to at least partly penetrate the penetrable region and the means to withdraw the penetrator from the penetrable region, may be enclosed.

Suitably the apparatus also comprises means to evaporate the carrier liquid out of the container via the conduit. Such means may comprise a conventional vacuum chamber as used in conventional lyophilization processes to apply reduced atmospheric pressure to the liquid in its frozen state.

Suitably the apparatus also comprises means to return the pressure to atmospheric by the ingress of a sterilized atmosphere when the evaporation operation is completed.

Suitably the apparatus also comprises means for providing a penetrable region by forming a puncture hole in the envelope. For example such means may comprise a hollow filling needle which can be passed through the envelope, for example through the elastomer closure of a vial, and via which the dispersion may be filled into the vial, and which can be subsequently withdrawn. Such means may be as discussed above.

Therefore a preferred sequence of operations for the process of this invention is firstly to introduce the liquid into the container, then to penetrate the penetrable region with the penetrator, then to reduce the temperature of the liquid in the container until it is frozen, then to evaporate the frozen liquid to thereby lyophilize the content, then to allow the temperature of the closure to rise toward ambient temperature, then to return the pressure toward atmospheric, then to withdraw the penetrator.

Preferably in a subsequent step of the process the residual hole through the penetrable region left by the penetrator is sealed. This may be achieved in various ways. For example in one way the material of the envelope, e.g., the vial closure, may be melted, e.g., by application of heat or other radiation and allowed to cool and set.

Such a process is for example disclosed in U.S. Pat. No. 2002/0023409 and WO-A-2004/026735. Additionally or alternatively a cover means may be attached to the container to close the site where the penetrator has penetrated the container. Alternate sealing means may be used, for example fixing a sealing means such as a patch or fluid substance which subsequently sets, to the penetration site. It may be advantageous to remove the above-mentioned removable guide, if used, from the container before this sealing operation. The containers may be transferred by suitable means such as a conveyor to a station where a sealing operation may be performed to seal the penetration site.

After sealing the residual hole through the penetrable region left by the penetrator, if the container is a vial of the type disclosed in WO-A-2004/018317 a cover part as disclosed therein may be engaged with the vial to cover the now-sealed penetrable region.

Suitably the apparatus also comprises means for sealing the residual hole through the penetrable region left by the penetrator, which may be achieved in various ways, as discussed above. Such means may comprise a means to direct laser radiation at the site of the residual hole.

Suitably, if the container is a vial of the type disclosed in WO-A-04/018317 the apparatus may comprise means to engage a cover part with the vial to cover the sealed penetrable region.

Therefore an overall process of the invention may comprise the steps of:

introducing a dispersion of the material in a carrier liquid into a vial closed by an elastomer closure by passing a hollow filling needle through the elastomer closure and introducing the liquid through the needle, then withdrawing the needle to leave a residual puncture hole through the closure;

penetrating the elastomer closure with a penetrator such that the penetrator provides a conduit through the envelope to provide communication between the inside and outside of the container when the penetrator has penetrated the penetrable region;

reducing the temperature of the liquid so that the liquid freezes solid;

evaporating the carrier liquid out of the container via the conduit by means of reduced atmospheric pressure;

causing the temperature of the elastomer closure to rise toward, preferably to, ambient and preferably re-pressurizing the inside of the vial with a sterile atmosphere;

withdrawing the penetrator from the penetrable region, then preferably sealing the residual puncture hole.

In a further aspect the invention provides a container suitable for use in a process or apparatus of the first embodiment as described above, having a penetrator moveably mounted thereon, e.g., on a vial, the penetrator being moveable reciprocally from a first position in which the penetrator is outside the container and does not penetrate the penetrable region, to a second position in which the penetrator penetrates the penetrable region such that the penetrator provides a conduit through the envelope to provide communication between the inside and outside of the container when the penetrator has penetrated the penetrable region, and preferably back toward a first position in which the penetrator is outside the container and does not penetrate the penetrable region.

In this last-mentioned apparatus the penetrator may be as described for the preceding aspects of the invention, and may be mounted on a guide as described above. For example in an embodiment particularly suitable for container being a vial, and the above-mentioned tubular or conical penetrator, the guide may comprise a generally cylindrical sleeve or part sleeve within which the penetrator is reciprocally movable.

Suitable and preferred features of such a container having a penetrator moveably mounted thereon are as discussed above.

The invention also provides the use of such a container having a penetrator moveably mounted thereon in a process and apparatus of the first and second aspects of this invention.

Figure 2:
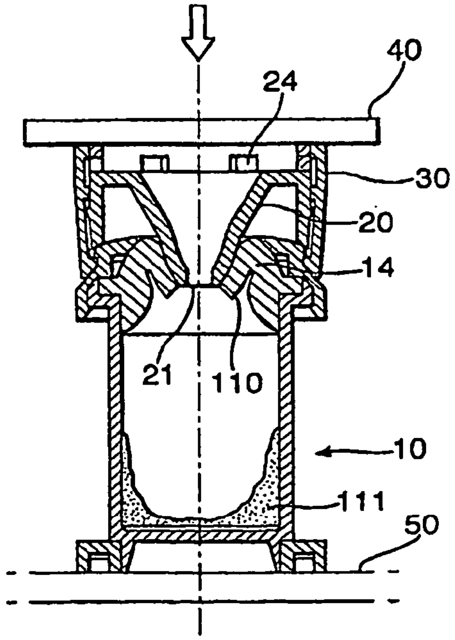

The invention will now be described by way of non-limiting example only with reference to the accompanying drawings which show:

FIGS. 1 and 2. A vial with a penetrator in first and second positions.

FIG. 3. An overall schematic process.

FIG. 4. A vial on a lower shelf and a upper shelf comprising penetrators.

FIG. 5. A schematic view of an arrangement according to FIG. 4.

FIG. 6. A schematic view of an alternative arrangement according to FIG. 4.

Figure 7:
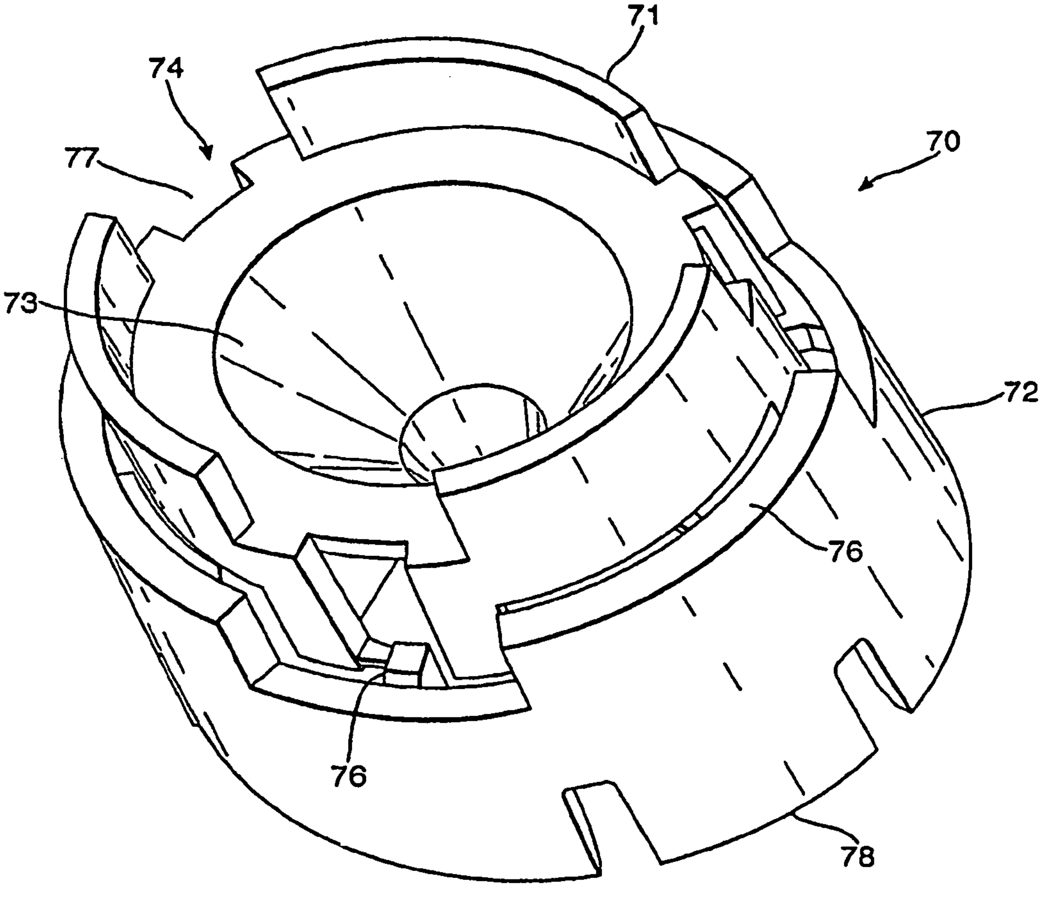

FIG. 7. A perspective view of a combination of penetrator and guide.

Figure 9:
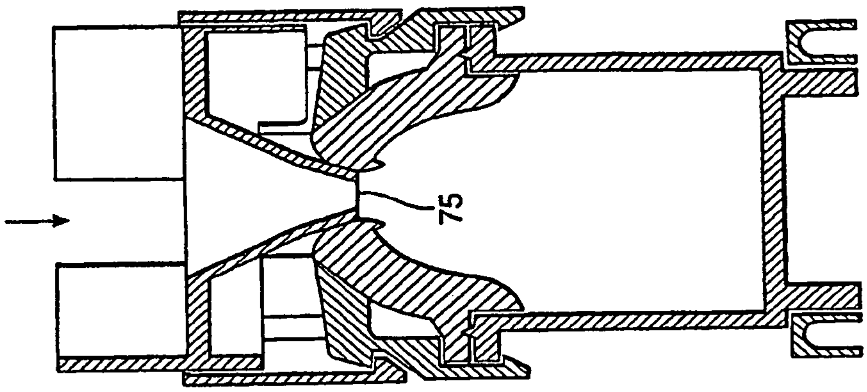
Figure 8:
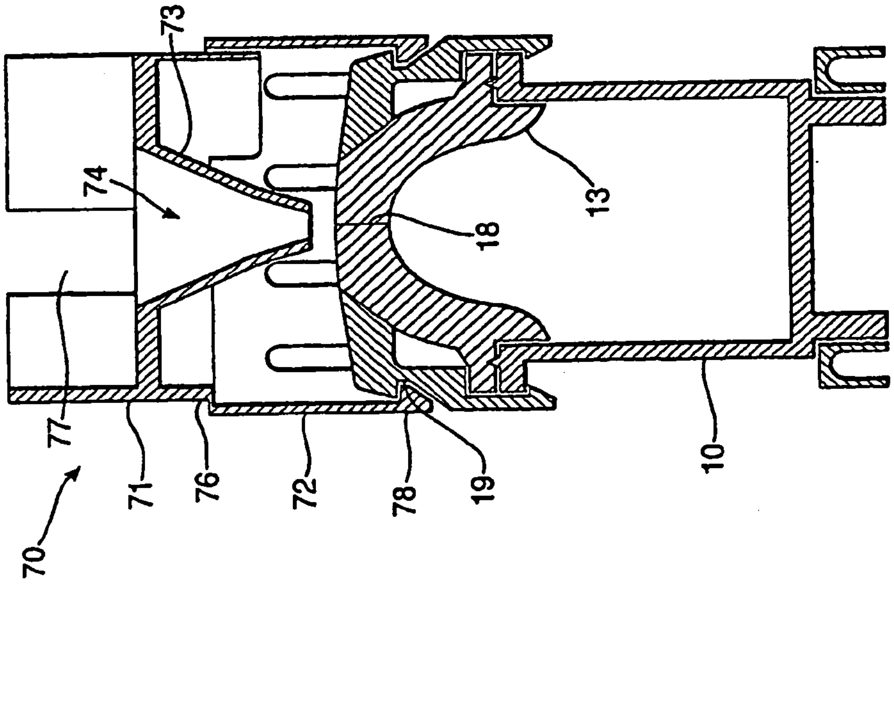

FIGS. 8 and 9. Two sectional views of the combination of FIG. 7.

Figures 10, 11, 12:
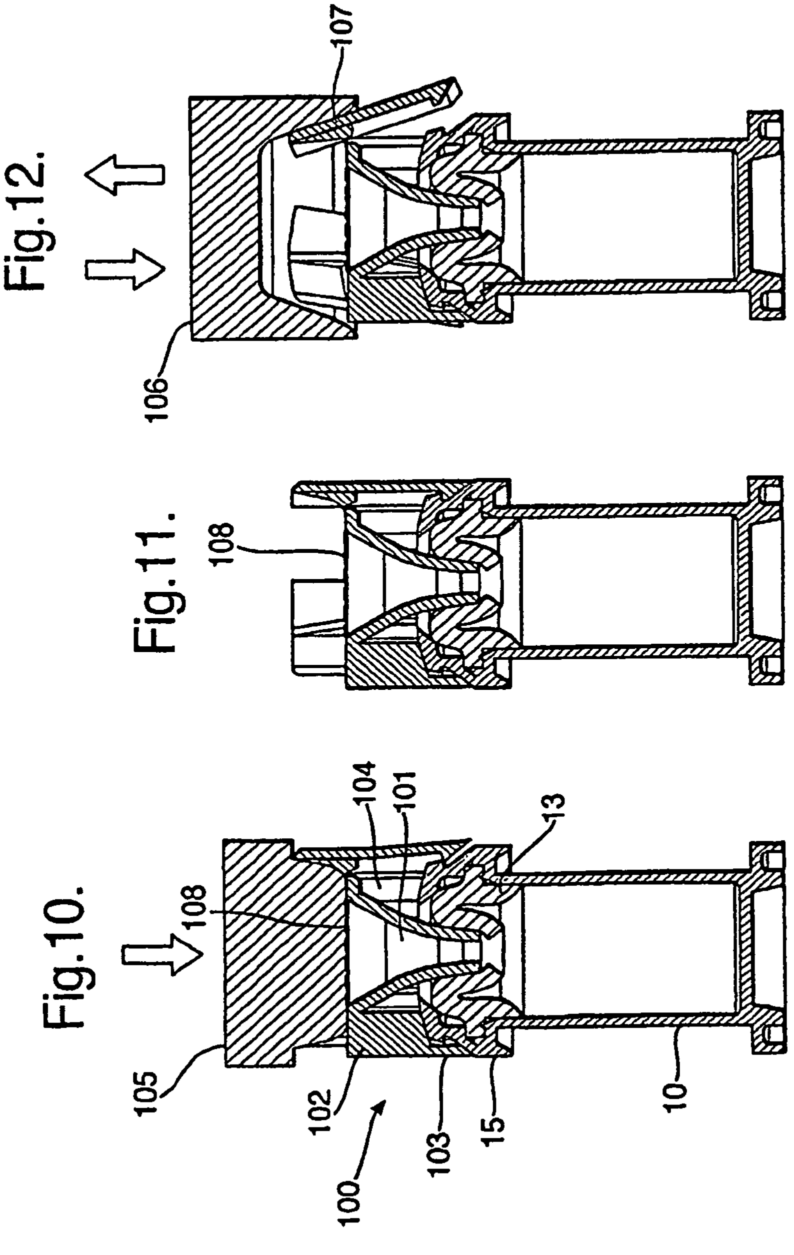

FIGS. 10, 11 and 12. Sectional views of a penetrator mounted on a vial.

Referring to FIGS. 1 and 2, a pharmaceutical vial 10 is shown in longitudinal section, being a vial of the type disclosed in WO-A-04/018317. This vial 10 comprises a generally cylindrical body 11 made of a clear plastics material having an upper mouth 12, which is closed by an elastomer plug closure 13 having an upper domed region 14. The closure 13 is held in place on the vial body 11 by a plastics material clamp part 15, which snap fits over the flange 16 of vial body 10. The combination of vial body 10 and plug closure 13 comprise an envelope as referred to herein.

The vial 10 contains an aqueous solution 17 of a vaccine material to be lyophilized after subsequently being frozen into a solid plug by reducing its temperature. The closure 13 has a puncture hole 18 passing completely through it. The solution 17 has been previously introduced into vial 10 by a process of radiation sterilizing the interior of the vial 10, passing a hollow filling needle (not shown) through the closure 13, introducing the solution 17 into the vial 10 via this needle, then subsequently withdrawing the needle to leave the puncture hole 18. The closure 13 is sufficiently elastic that after the needle has been withdrawn the elastomer material of the closure springs together to physically close the puncture hole 18 by compressing the sides of the hole 18 together.

A penetrator 20 is shown moveably mounted on the vial 10. Penetrator 20 comprises a generally hollow conical member with its apex pointing downwardly toward the upper outer surface of the closure 13. The conical member 20 has an opening 21 at its apex with a narrowest cross section ca. 2 mm, and has an open base and has a hollow interior. The conical member 20 is moveably mounted on the vial 10 by means of the member 20 being reciprocally moveable within a cylindrical guide 30 which is removably mounted on the clamp part 15, by means of the guide 30 having a snap fit bead 31 adjacent its lower end which can snap-fit engage with a groove 19 in the outer surface of the clamp part 15. To facilitate the reciprocal movement of the member 20 within the guide 30 the member 20 is integrally provided with an outer collar 22 which is a close conforming sliding fit inside guide 30.

The penetrator 20 can be moved reciprocally from a first position seen in FIG. 1 in which the penetrator 20 is outside the vial 10 and does not at least partly penetrate the penetrable region 14 of the closure 13. In this position the penetrator 20 is resting on the upper surface of the part 14, adjacent to the puncture hole 18. The penetrator 20 is moveable from this first position to a second position seen in FIG. 2 in which the apex of the penetrator 20 at least partly penetrates the penetrable region 14 of the closure 12.

The penetrator 20 has been moved from the first position shown in FIG. 1 into the second position seen in FIG. 2 by means of the member 40 which is situated above the assembly of vial 10, penetrator 20 and guide 30. In practice plural vials 10 are arranged in a two dimensional array on a first shelf 50, and further shelves of vials 10 (not shown) are stacked vertically shelf 50. The member 40 comprises part of a vertically adjacent shelf which bears upon the penetrator 20 to urge the penetrator 20 into the second position shown in FIG. 2. This may be achieved by loading the shelves 40, 50 into a rack (not shown) which supports them with a vertical spacing to achieve this. The collar 22 of penetrator 20 has an upper part 23 with apertures 24 therein in communication with apertures (not shown) in guide 30. A barrier membrane 25 which is permeable to gases but obstructs the passage of particles is provided across the open base of the conical member 20. Additionally the upper rim of part 23 may be castellated.

As is seen in FIG. 2 in this position the pointed apex of the penetrator 20 has partly penetrated the domed upper part 14 of the closure 13 by forcing open the puncture hole 18, and forcing apart the parts of the elastomer of the closure immediately adjacent to the puncture hole 18. These adjacent elastomer parts 110 are forced toward the interior of the vial 10. In the position shown in FIG. 2 the opening 21 and the hollow interior of the conical member 20 and apertures 24 comprise a conduit between the interior of the vial 10 and the exterior.

In the configuration shown in FIG. 2 the assembly of vial 10, penetrator 20 and guide 30 have been cooled to a temperature which maintains the solution 17 frozen solid and then exposed to a reduced atmospheric pressure. The carrier liquid of solution 17 has evaporated by sublimation, its vapor escaping through the conduit formed by the opening 21 and the hollow interior of the conical member 20 and apertures 24, until the vaccine dissolved therein is left as a lyophilized solid 111.

When the lyophilization process is completed the interior of the vial 10 can be re-pressurized by allowing a sterile gas such as air to enter the vial.

The shelf 40 is then raised, i.e., to a position corresponding to FIG. 1. The elasticity of the elastomer material of the closure 13 is employed to move the penetrator 20 back toward a first position corresponding to FIG. 1. The elastic nature of the closure tends to close the penetration hole seen in FIG. 2 resulting from the penetration by the penetrator 20 and tends to force the penetrator 20 toward the position shown in FIG. 1. The force applied to the penetrator 20 and the restraint of movement of the penetrator 20 by the upper shelf 40 maintains the penetrator 20 in the position shown in FIG. 2 extending through the elastic closure 13. When the shelf is raised away from the penetrator 20 this force and restraint is released and the elasticity of the closure 13 springs the penetrator back into the first position as shown in FIG. 1. Also the elasticity of the closure 13 physically closes the puncture hole 18.

Thereafter the guide 30 may be detached from the vial 10. The residual hole 18 through the closure 13 may be sealed, which may for example be achieved by the known process of directing a beam of laser radiation at the puncture hole 18 to melt the adjacent elastomer material and subsequently allow the molten material to set and seal the puncture site. A cover part (not shown) may then be engaged with the clamp part 15 to cover the now-sealed penetrable region 18.

An alternative construction (not shown) of penetrator 20 may have a conical member 20 with a pointed apex, but with one or more external concavity, e.g., groove which when the member 20 is in a position corresponding to FIG. 2, form a conduit between the sides of the hole 18 and the penetrator 20 through which the carrier liquid of the solution 17 can escape.

FIGS. 3A to 3M schematically show an overall process.

Figure 3A:
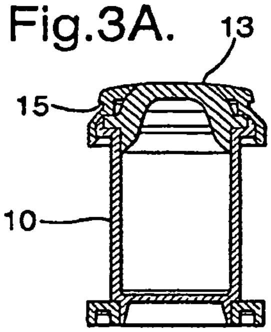

In FIG. 3A an empty vial 10 with its closure 13 and clamp part 15 is shown, its interior being sterile as a result of radiation sterilization or sterile manufacture.

Figure 3B:
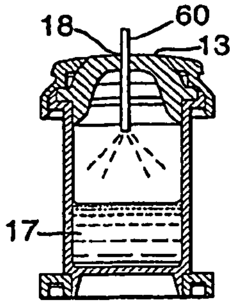

In FIG. 3B a filling needle 60 is passed through closure 13, creating a puncture hole 18, and the solution 17 of a material to be lyophilized is introduced into vial 10 via needle 60.

Figure 3C:
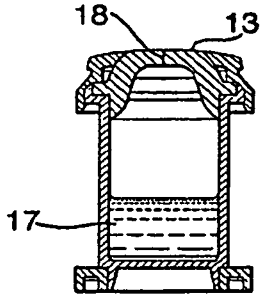

In FIG. 3C the filling needle 60 has been withdrawn from the closure 13, leaving the residual puncture hole 18, which is closed by the adjacent elastomer material of closure 13 springing back under its elasticity.

Figure 3D:
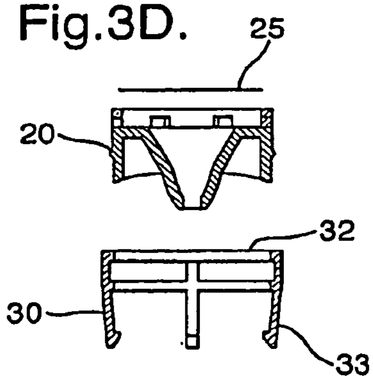

In FIG. 3D the penetrator 20, the guide 30 and the membrane 25 are assembled. FIG. 3D shows a guide 30 which is a part cylindrical sleeve comprising an upper ring-shaped frame 32 and lower resilient snap-fit legs 33.

Figure 3E:
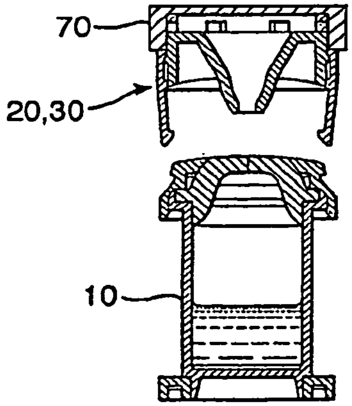
Figure 3F:
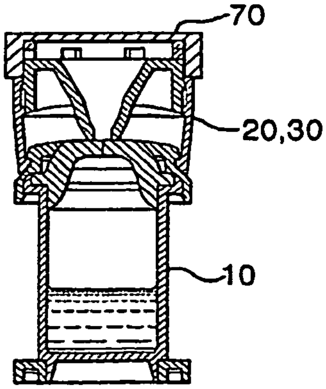

In FIGS. 3E and 3F a fitting tool 70 is used to engage the combination of penetrator 20 and guide 30 with the vial 10 containing the solution 17.

Figure 3G:
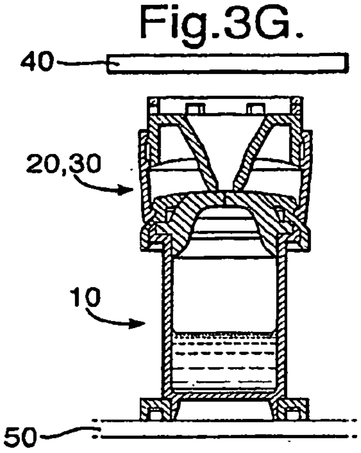

In FIG. 3G the fitting tool 70 has been disengaged from the assembly 20, 30, and the vial 10 plus the assembly 20, 30 has been arranged on a lower tray 50, with an upper tray 40 spaced vertically above with a similar array of vials 10 (not shown) thereon. The penetrator 20 is resting on the top of the closure 13.

Figure 3H:
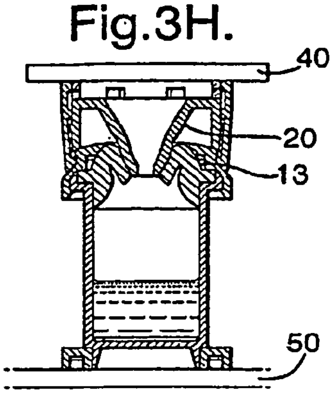

In FIG. 3H the shelf 40 is lowered relative to the lower shelf 50, and bears on the penetrator 20, as in FIG. 2. The penetrator 20 at least partly penetrates closure 13, elastically forcing back the elastomer material of the closure adjacent the puncture hole 18.

Figure 3I:
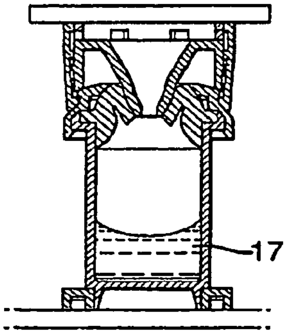

In FIG. 3I with shelves 40, 50 in the same configuration as in FIG. 3H the temperature has been reduced so that the solution 17 is frozen solid.

Figure 3J:
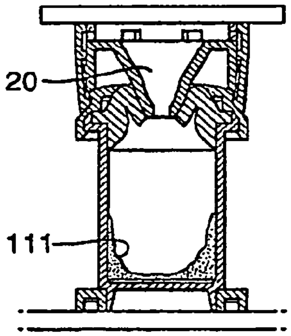

In FIG. 3J the frozen solution 17 has been exposed at the reduced temperature to a reduced atmospheric pressure so that the vapor of the frozen liquid of the solution 17 sublimates out through the penetrator 20 to leave the material as a dry lyophilized solid 111.

Figure 3K:
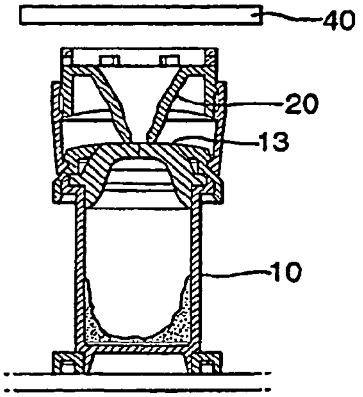

In FIG. 3K the lyophilization process is complete, all the liquid has sublimed from the frozen solution 17, the vial has been re-pressurized with a sterile atmosphere, e.g., nitrogen, and the temperature of the vial 10 and its closure has been allowed to rise to ambient. Shelf 40 has been lifted from its position of bearing on penetrator 20 so that the elasticity of the closure 13 springs the penetrator 20 upwards toward the first position.

The steps shown in FIGS. 3G to 3K may take place inside a generally conventional lyophilization freeze-drier, and the lowering and raising of shelves 40 may be performed by generally conventional machinery.

Figure 3L:
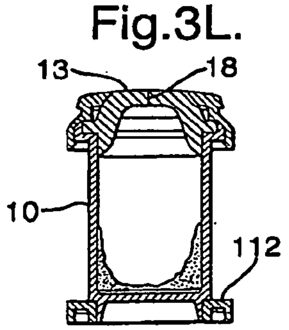

In FIG. 3L the assembly 20, 30 has been disengaged from vial 10. A de-fitting tool (not shown) may be used for this purpose, and conveniently the vials 10 have a lower flange 112 allowing a holding means (not shown) to hold the vial down against the upward pulling force of such a de-fitting tool. The elasticity of closure 13 again causes the puncture hole 18 to close.

Figure 3M:
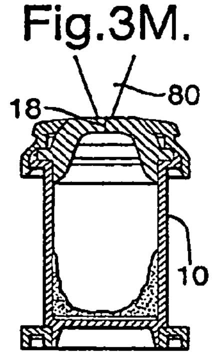

In FIG. 3M a laser beam 80 has been directed at the elastomer material adjacent to puncture hole 18 to seal this hole, as described above.

From FIG. 3 it can be seen that at no time after the vial 10 has been filled until the vial 10 is in the lyophilization chamber is the vial 10 open to the environment where it might be contaminated. Also the vials as at FIG. 3C may be inspected for particulate contamination without fear of further contamination, as the elasticity of the closure 13 holds the puncture hole 18 closed.

Suitable conveyors etc. may be used to transport the vials 10 through this process, and suitable automatic machinery may be used to assemble the parts 20, 30 and to engage this assembly with the vials 10. The stack of shelves 40, 50 may be moved up and down vertically by known means, e.g., hydraulically. The parts 20, 30 may be re-usable after suitable cleaning and sterilization.

Figures 4A, 4B, 4C:
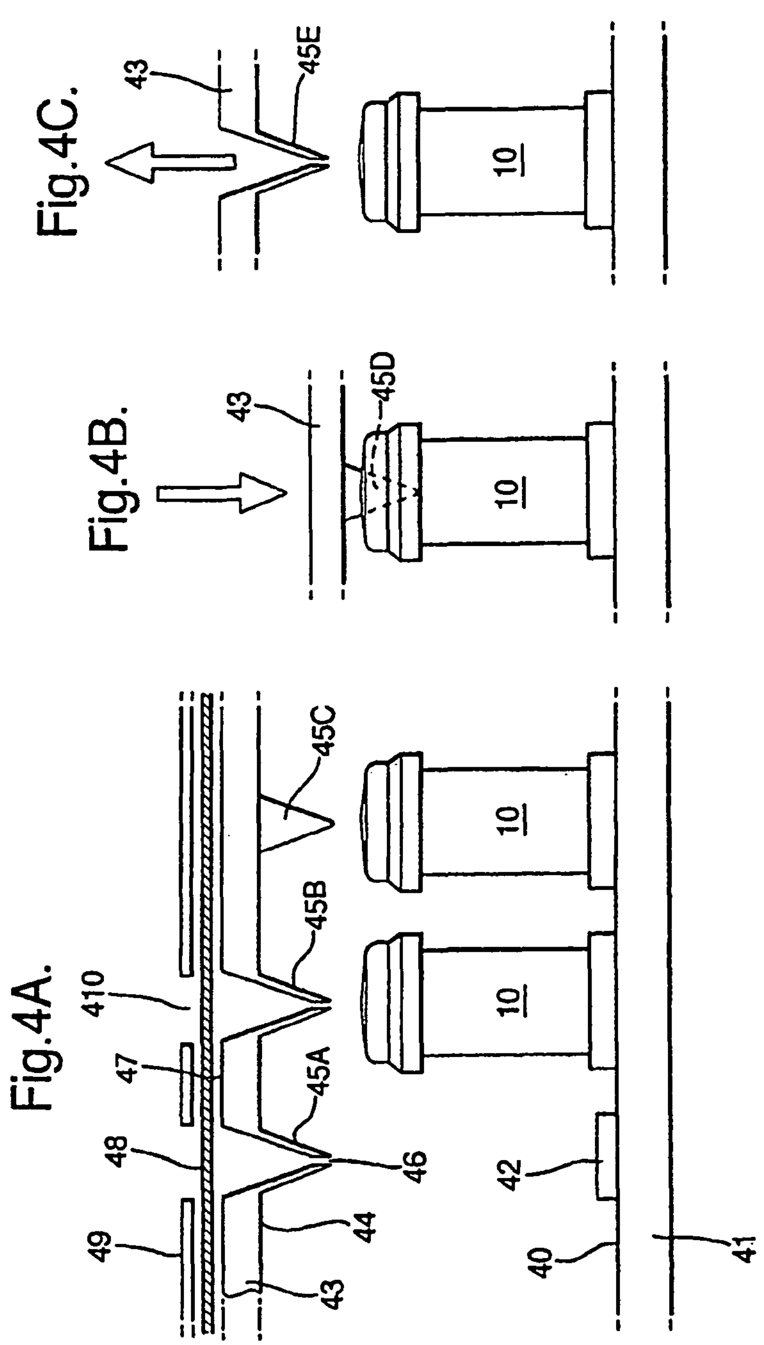

FIGS. 4 and 5 illustrate a process of the second embodiment and a suitable apparatus. Referring to FIG. 4 plural vials 10 of the type disclosed in WO-A-04/018317 are shown. The vials 10 are situated on an upward facing surface 40 of a lower shelf 41. The surface 40 is provided with centering plugs 42, typically cones, which fit into a corresponding socket in the base of vials 10 to securely locate the vials 10 in a predetermined position on shelf 40. There is a vertically adjacent upper shelf 43. Shelves 41, 43 are made of metal, e.g., stainless steel. Extending from the lower surface 44 of upper shelf 43 are plural penetrators 45A, 45B, 45C, 45D, 45E. Each penetrator 45A, 45B, 45C, 45D, 45E comprises a generally conical member with its apex pointing downwardly from the lower surface 44 of the upper shelf 43 toward the lower shelf 40. Penetrators 45A, 45B, 45C, 45D and 45E are each a hollow cone with a hole 46 adjacent its apex, with an open base such that its apex may penetrate the penetrable region of closure 13 of a vial 10 and vapor of the carrier liquid may enter the apex, pass through the hollow interior of the cone and exit via the open base analogously as described above. Penetrators 45A, 45B and 45E are shown in section to illustrate their construction. Penetrators 45A, 45B, 45C, 45D and 45E are made integrally of metal with the upper shelf. Above and in contact with the upper surface 47 of shelf 43 is a sterile filter sheet 48 which can allow gases to pass through but prevents passage of particles, and filter sheet 48 is itself held in place by an upper plate 49 with apertures passing through corresponding to the positions of the open bases of the penetrators 45A-E. In FIG. 4A penetrators 4A-C are in a first position in which the penetrators 4A-C are outside vials 10 and do not penetrate the closures 13 of vials 10. In FIG. 4A the penetrators 45B, 45C are in a position analogous to the penetrators 20 in FIG. 3G.

FIG. 4B shows how upper shelf 43 is moved downwardly relative to lower shelf 41 into a second position in which penetrator 45D penetrates the closure 13 of vial 10. In this position the hollow interior of the penetrator 45D allows vapor of frozen carrier liquid to escape from vial 10 via hole 46 and the open base of the cone. In FIG. 4B the penetrator 45D is in a position analogous to the penetrator 20 in FIG. 3H-3J.

FIG. 4C shows how the upper shelf 43 is then returned back into a first position in which the penetrator 45E is outside the vial 10 and does not penetrate the closure 13. In FIGS. 4B and 4C the filter 48 and plate 49 are omitted for clarity. In FIG. 4C the penetrator 45B is in a position analogous to penetrators 20 in FIG. 3G.

Figure 5A:
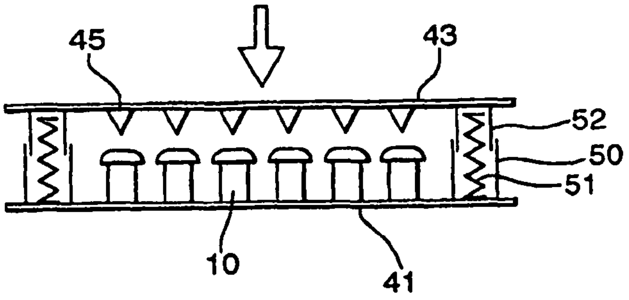
Figure 5B:

Referring to FIG. 5 an arrangement of a lower shelf 41 with vials 10 thereon, i.e., as shown in FIG. 4 is shown. In FIG. 5A the upper shelf 43 is raised so that penetrators 45 are in their first position, i.e., as in FIGS. 4A and 4C. In FIG. 5B the upper shelf 43 is in its lower position so that penetrators 45 are in their second position as shown in FIG. 4B. The upper and lower shelves 41, 43 are biased into this second position as shown in FIG. 5A by springs 50 positioned within telescoping tubular housings 51, 52. In FIG. 5B springs 50 are in their compressed state. In the arrangement shown in FIGS. 4 and 5 vials 10 may be positioned on the lower shelf 41 with the upper shelf 43 absent, then the upper shelf 43 maybe positioned over lower shelf 41. The telescoping spring housings 51, 52 help to position the penetrators 45 over vials 10 and guide the penetrators 45 toward vials 10 as the upper shelf 43 is lowered toward the lower shelf 41 against the bias of springs 50. The upper shelf 43 may be held in the position shown in FIG. 5B against the bias of springs 50 during the step of evaporating the frozen carrier liquid out of the vials 10 by a suitable means, e.g., a stop.

Referring to FIG. 6 the upper shelf 43 has an upward facing surface 60 on which are situated plural vials 10 in a manner analogous to that in FIGS. 4 and 5. Vertically adjacent to this upper shelf 43 there is a further upper shelf 61 which comprises plural penetrators 451 above this upward facing surface. The shelves 43 and 61 are biased apart by springs 62 positioned within telescoping tubular housings 63, 64 in a manner analogous to FIG. 5. This further upper shelf 61 may be moved downwardly toward shelf 43 analogously to the way shelf 43 may be moved downwardly toward lower shelf 41 as described above with reference to FIG. 5. The further upper shelf 61 may itself have an upward facing surface 65 on which are situated plural vials (not shown), so that plural such shelves may be stacked vertically relative to each other.

The arrangement shown in FIGS. 4-6 can be used in a process analogous to FIG. 3. Vials 10 containing a solution of a material to be lyophilized may be positioned on lower shelf 41 and upper shelf 43 may be positioned as shown in FIGS. 4A and 5A. Upper shelf 43 may then be lowered, e.g., against the bias of springs 50, into the position as shown in FIGS. 4B and 5B so that penetrators 45 penetrate the closures 13 of vials 10. The carrier liquid in the vials 10 may then be frozen by exposure to reduced temperature. The frozen carrier liquid may then be evaporated out of vials 10 via the penetrators 45. The vials 10 may then be re-pressurized with a sterile atmosphere such as nitrogen and their temperature allowed to rise toward ambient. Then the upper shelf 43 may be raised relative to the lower shelf 41 so that the shelves 43, 41 are in the position shown in FIGS. 4C and 5A.

Thereafter the vials 10 may be removed from lower shelf 41 and the residual puncture hole 18 in the closure 13 sealed with a focused laser beam as in FIG. 3M.

The process and apparatus illustrated in FIGS. 3, 4, 5 and 6 is suitably respectively performed and located inside a sterile enclosure the temperature of which can be controlled between ambient and a temperature at which the carrier liquid is frozen, and the atmospheric pressure of which can be controlled between ambient and a reduced atmospheric pressure.

Referring to FIGS. 7, 8 and 9 a combination 70 of a penetrator 71 and a guide 72 is shown, in FIGS. 8 and 9 being shown mounted on a vial 10. The penetrator 71, as seen more clearly in FIGS. 8 and 9 comprises a generally conical member 73, with a hollow interior 74 and an opening 75 at its apex. The apex of this conical shaped member is adapted to penetrate a penetrable region, being puncture hole 18 in an elastomeric closure 13 of vial 10. The penetrable region of the closure 80 comprises a residual puncture hole (not shown) which has been made by a filling needle (not shown) used to introduce a liquid content (not shown) for lyophilization into the vial 81.

The guide 72 comprises a generally cylindrical sleeve within which the penetrator 71 is mounted. As shown in FIG. 8 the penetrator 71 is in its first position, with the apex 75 of the conical penetrator 73 pointed downwards as seen, the penetrator 71 not penetrating the closure 13, and with ca. 1 mm space between the apex 75 of the penetrator 71 and the upper (as seen) surface of the closure 13.

The penetrator 71 and guide 72 are made integrally of plastics material, and are so made initially linked by plural (six are shown there may be more or less) thin frangible integral links 76 with the penetrator in its first position as shown in FIG. 8.

As shown in FIG. 9 the penetrator 71 has been moved analogously as shown in FIGS. 1 and 2 towards a second position so that the penetrator 71 thereby penetrates the closure 13, opening the residual puncture hole 18. Severance of the links 76 occurs. The liquid content of vial 10 is not shown in FIGS. 8 and 9.

The penetrator 71 has an upper rim with openings 77 corresponding to the vents 24 of FIG. 1. The guide 72 is removably mounted on vial 10 by a snap-fit connection analogous to that of FIG. 1, using the resilient fingers 78 which engage with the groove 19 of vial 10. A barrier membrane analogous to that 25 of FIG. 1 which is permeable to gases but obstructs the passage of particles may be provided across the open base of the conical member 73.

Referring to FIGS. 10, 11 and 12 a penetrator 100 is shown mounted on a vial 10 of the type previously shown. Penetrator 100 comprises a generally conical member 101 analogous to the penetrators exemplified above, and made of plastics material by means of injection molding. The penetrator 100 is mounted on the clamp part 15 of the vial 10 by means of a snap fit engagement. This snap-fit engagement is provided by a skirt 102 extending in the cone base-apex direction and surrounding the conical member 101, the skirt 102 having snap-fit engagement fingers 103 means adjacent the rim furthest from the cone base which engage, as above, with a groove on the clamp part 15. The conduit 104 through the conical member 101 of the penetrator is closed by a barrier membrane 108, e.g., as shown across the open base of the hollow conical interior which allows gases to pass through but not particulate contaminants. The barrier membrane prevents the ingress of contaminants into the interior of the vial 10 through the conduit 104 of the penetrator 100.

As shown in FIGS. 10, 11 and 12 the penetrator 100 is mounted on the vial 10 in a position in which the penetrator is penetrating the residual puncture hole (not shown) in the elastomeric closure 13 of the vial 10 in a manner analogous to the above. The mounting is achieved by means of mounting tool 105 bearing downwards upon the penetrator 100 to operate the snap-fit engagement.

With the penetrator 100 and vial 10 in the configuration shown in FIG. 11, frozen liquid content (not shown) in vial 10 can be evaporated out through the conduit 104, as above.

When the evaporation is complete the penetrator 100 is removed from the vial 10. This is achieved as shown in FIG. 12 by means of a removal tool 106 which bears upon the upwardly extending part of pivot lever 107, the operation of which in relation to one of the fingers 103 is shown, to thereby disengage the snap-fit engagement. The elasticity of the closure 13 can then spring the penetrator out of its penetrating relationship with the closure 13.

We claim:

1. A process for lyophilizing a substance present in a carrier liquid comprising:

providing a container closed by a closure made of elastomeric material having an elasticity, said elastomeric material having a penetrable region with a previously-formed puncture hole which is closed at a rest stage of the closure;

providing a penetrator having an engaging end;

moving the penetrator from a first position where the penetrator contacts said material at said previously-formed puncture hole to a second position so that during the movement its engaging end opens said previously-formed puncture hole so as to form an opening communication passage;

stopping the movement of the penetrator at the second position so that its engaging end stops just before entering into the material of the closure and maintaining the penetrator in said second position by applying a compensating force in order to compensate for the elasticity of said elastomeric material;

evaporating the carrier liquid of the substance from the container via the opening communication passage by maintaining the substance in the carrier liquid at a temperature such that the carrier liquid is frozen, and by applying reduced pressure so that the frozen liquid sublimates directly from the solid to the vapor state; and releasing said compensating force applied on the penetrator and withdrawing the penetrator from the elastomeric penetrable region.

2. The process according to claim 1 performed in the following order:

introducing the dispersion of the material in a carrier liquid into the container;

penetrating the penetrable region with the penetrator;

reducing the temperature of the liquid in the container until it is frozen;

evaporating the frozen liquid to thereby lyophilize the content;

allowing the temperature of the container to rise toward ambient temperature;

returning the pressure toward atmospheric; and withdrawing the penetrator.

3. The process according to claim 1 wherein the container is a vial with an elastomeric closure, the penetrable region comprises a puncture hole in an elastomer vial closure, and wherein the process further comprises sealing the residual puncture hole.

* * * * *